(12) United States Patent
Shiraki et al.

(10) Patent No.: US 9,006,434 B2
(45) Date of Patent: Apr. 14, 2015

(54) CRYSTALS OF GLYCINE DERIVATIVE AND PHARMACEUTICAL USE THEREOF

(75) Inventors: Motohiro Shiraki, Kamakura (JP); Hirozumi Takahashi, Kamakura (JP); Tsutomu Nogami, Mishima (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/129,166

(22) PCT Filed: Jun. 29, 2012

(86) PCT No.: PCT/JP2012/066672
§ 371 (c)(1),
(2), (4) Date: Dec. 24, 2013

(87) PCT Pub. No.: WO2013/002364
PCT Pub. Date: Jan. 3, 2013

(65) Prior Publication Data
US 2014/0128605 A1  May 8, 2014

(30) Foreign Application Priority Data

Jun. 30, 2011 (JP) ................. 2011-145446

(51) Int. Cl.
*C07D 239/42* (2006.01)

(52) U.S. Cl.
CPC .................. *C07D 239/42* (2013.01)

(58) Field of Classification Search
CPC .................................................. C07D 239/42
USPC ........................................................ 544/332
See application file for complete search history.

(56) References Cited

U.S. PATENT DOCUMENTS 4,521,431 A    6/1985   Crookes

FOREIGN PATENT DOCUMENTS

| JP | 57-91983 A | 6/1982 |
| WO | 99/01444 A1 | 1/1999 |
| WO | 2006/068213 A1 | 6/2006 |
| WO | 2007/145282 A1 | 12/2007 |
| WO | 2007/148648 A1 | 12/2007 |
| WO | 2007/148676 A1 | 12/2007 |
| WO | WO 2014/051056 * 4/2014 ........... C07D 239/42 |

OTHER PUBLICATIONS

"4.3.3 Recrystallization of Organic Compounds," *The Chemical Society of Japan*, Jun. 10, 1985, pp. 318-322 with partial English translation.

* cited by examiner

*Primary Examiner* — Erich A Leeser
(74) *Attorney, Agent, or Firm* — DLA Piper LLP (US)

(57) ABSTRACT

A crystal of (S,E)-2-(2,6-dichlorobenzamido)-5-[4-(methyl-pyrimidin-2-ylamino)phenyl-yl]pent-4-enoic acid has excellent chemical and physical stability, and a medical use thereof.

10 Claims, 5 Drawing Sheets

CRYSTALS OF GLYCINE DERIVATIVE AND PHARMACEUTICAL USE THEREOF

TECHNICAL FIELD

This disclosure relates to a crystal of glycine derivative and a medical use thereof.

BACKGROUND

Pharmaceuticals are required to maintain the quality thereof for a long time during distribution, storage and the like, and high chemical and physical stability is demanded for compounds as effective components. Thus, for the effective components of pharmaceuticals, crystals which are expected to have high stability compared to amorphous products are commonly employed.

In screening the crystals of effective components of pharmaceuticals, it is difficult to find optimal conditions to obtain the crystals, and also even when the crystals can be obtained, the existence of crystalline polymorphs is problematic in many cases. This is because each crystal form has a different molecular packing arrangement in spite of the same chemical structure in the molecular unit, so that there are differences in chemical and physical stabilities between the crystal forms.

If the crystal form of a compound employed as an effective component of pharmaceuticals is selected incorrectly, the decrease in purity, change in hydration degree, change in crystal form and the like occur due to the external environment during storage, and it is difficult to maintain the quality of the compound, thereby resulting in unexpected situations such as the reduction in pharmacological effects and the occurrence of side effect depending on the crystal forms. Therefore, in cases where the crystals of the compound as an effective component of pharmaceuticals are successfully obtained, it is necessary to evaluate the crystalline polymorphs of the compound strictly.

On the other hand, (S,E)-2-(2,6-dichlorobenzamido)-5-[4-(methyl-pyrimidin-2-ylamino)phenyl]pent-4-enoic acid represented by Formula (I) below has been known to exhibit therapeutic effects on inflammatory bowel disease, allergic dermatitis, multiple sclerosis and leukemia (WO 2006/068213, WO 2007/145282, WO 2007/148648 and WO 2007/148676):

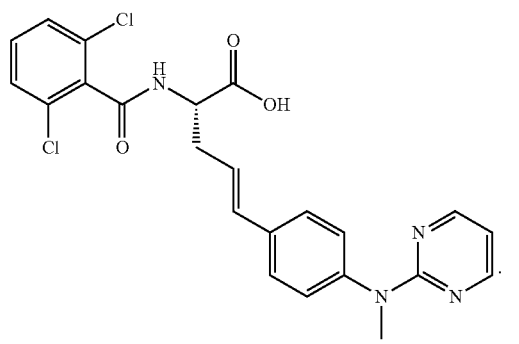

(I)

However, since it is impossible to predict the existence of crystalline polymorphs or stable crystal form from the chemical structure of the compound and, further, there may be a compound which cannot form a crystal, it is necessary to study conditions of forming a crystal for each compound in various ways. Although excellent effectiveness as an effective component of pharmaceuticals is confirmed for (S,E)-2-(2,6-dichlorobenzamido)-5-[4-(methyl-pyrimidin-2-ylamino)phenyl]pent-4-enoic acid, the existence of crystalline polymorphs or even the possibility of crystal formation have not been known at present, and to obtain the optimal crystal form was an important task for developing the compound as a pharmaceutical product.

It could therefore be helpful to provide a crystal of (S,E)-2-(2,6-dichlorobenzamido)-5-[4-(methyl-pyrimidin-2-ylamino)phenyl]pent-4-enoic acid having excellent chemical and physical stability, and a medical use thereof.

SUMMARY

We discovered crystalline polymorphs of Form A, Form B, Form C, From D and Form E (hydrate) of (S,E)-2-(2,6-dichlorobenzamido)-5-[4-(methyl-pyrimidin-2-ylamino)phenyl]pent-4-enoic acid and a plurality of solvate crystals. Among these, the crystals of Form B, Form C, Form D and Form E (hydrate) have low moisture absorption and excellent physical stability; the crystals of Form B, Form C and Form E (hydrate) have excellent chemical and physical stability under severe storage conditions; and the crystal of Form C has excellent physical stability even in an external environment in which the crystal is exposed to solvents.

That is, we provide a crystal described in the following (1) to (10) and a medical use thereof:

(1) A crystal of (S,E)-2-(2,6-dichlorobenzamido)-5-[4-(methyl-pyrimidin-2-ylamino)phenyl]pent-4-enoic acid.

(2) The crystal according to (1), which exhibits peaks at 2θ (°) of 17.1, 17.7, 18.7, 19.9 and 21.0° in powder X-ray diffraction.

(3) The crystal according to (2), which exhibits an endothermic peak in the range of 178 to 182° C. in thermogravimetric-differential thermal analysis.

(4) The crystal according to (1), which exhibits peaks at 2θ (°) of 5.9, 8.3, 11.8, 13.2 and 21.7° in powder X-ray diffraction.

(5) The crystal according to (4), which exhibits an endothermic peak in the range of 167 to 171° C. in thermogravimetric-differential thermal analysis.

(6) The crystal according to (1), which exhibits peaks at 2θ (°) of 6.6, 8.3, 11.1, 14.6 and 18.2° in powder X-ray diffraction.

(7) The crystals according to (6), which exhibit an endothermic peak in the range of 100 to 104° C. in thermogravimetric-differential thermal analysis.

(8) The crystal according to any one of (1) to (7), which is a non-solvate or a hydrate.

(9) A pharmaceutical comprising as an effective component the crystal according to any one of (1) to (8).

(10) A therapeutic or prophylactic agent for inflammatory bowel disease, allergic dermatitis, multiple sclerosis or leukemia, comprising as an effective component the crystal according to any one of (1) to (8).

Since the crystal is excellent in chemical and physical stability compared to the amorphous form, the crystal is preferable as an effective component of pharmaceuticals, and can contribute to the provision of highly reliable pharmaceuticals which suppress risks such as a decrease in pharmacological effects and occurrence of side effect.

DETAILED DESCRIPTION

The crystal is a crystal of (S,E)-2-(2,6-dichlorobenzamido)-5-[4-(methyl-pyrimidin-2-ylamino)phenyl]pent-4-enoic acid, and is characterized by the existence of crystalline polymorphs of Form A, Form B, Form C, From D and Form E (hydrate).

The crystal forms of (S,E)-2-(2,6-dichlorobenzamido)-5-[4-(methyl-pyrimidin-2-ylamino)phenyl]pent-4-enoic acid (hereinafter also referred to as "the subject compound") can be distinguished by characteristic peaks depicted in the powder X-ray diffraction patterns or endothermic peaks depicted in the differential thermal analysis curves (hereinafter referred to as "DTA curve") obtained by thermogravimetric-differential thermal analyses (hereinafter referred to as "TG-DTA"). The powder X-ray diffraction pattern and DTA curve may somewhat vary depending on the measurement conditions. For example, as for the diffraction angle 2θ in the powder X-ray diffraction, error of around ±0.2° is generally acceptable.

Figure 1:
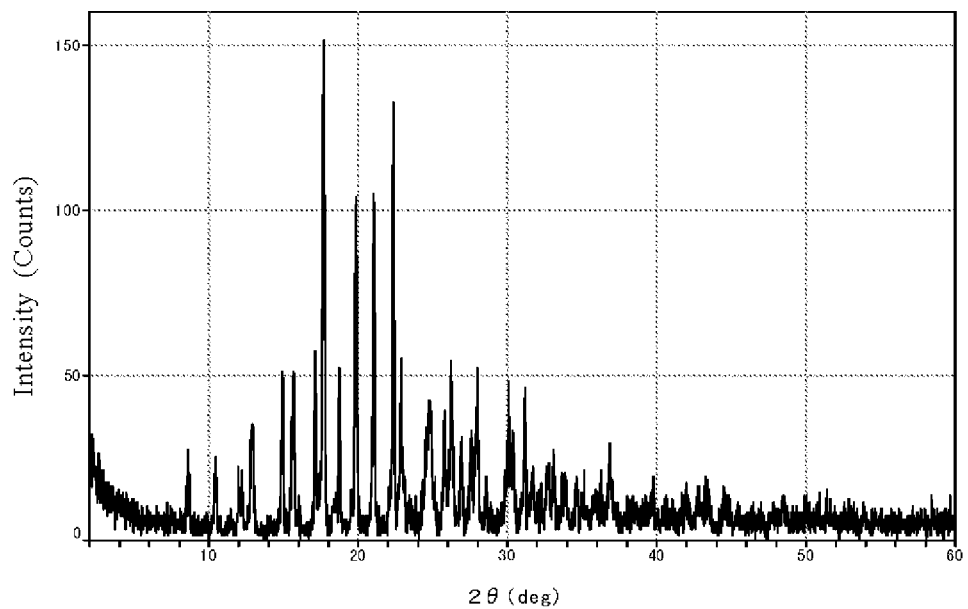
FIG. 1 is a powder X-ray diffraction pattern of the Form C crystal of the subject compound.

As shown in FIG. 1, the Form C crystal of the subject compound exhibits characteristic peaks at diffraction angle 2θ (°) of 17.1, 17.7, 18.7, 19.9 and 21.0° in powder X-ray diffraction. Also, the Form C crystal of the subject compound provides the DTA curve depicted in FIG. 2, and exhibits an endothermic peak at 180° C., that is 178 to 182° C.

Figure 3:
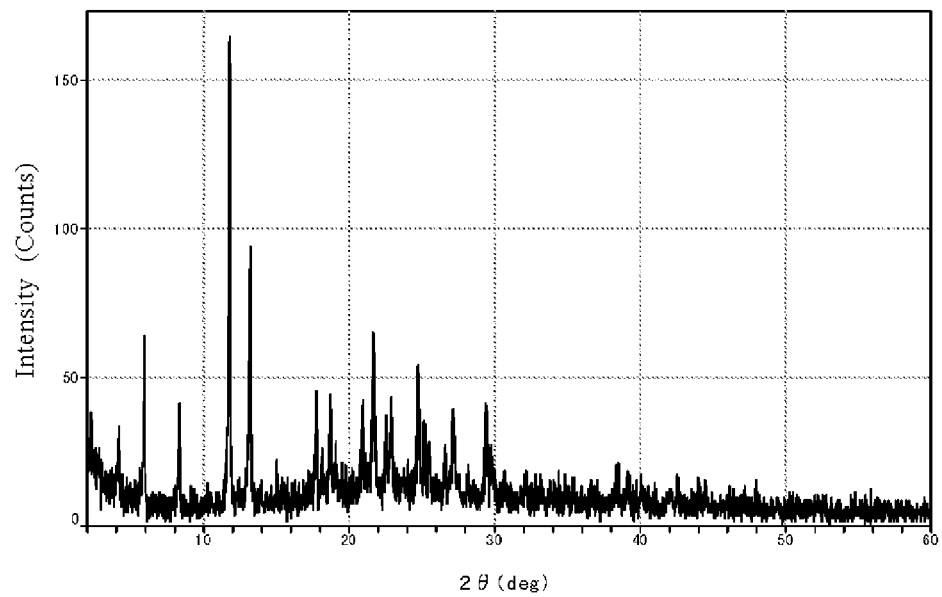
FIG. 3 is a powder X-ray diffraction pattern of the Form B crystal of the subject compound.

As shown in FIG. 3, the Form B crystal of the subject compound exhibits characteristic peaks at diffraction angle 2θ (°) of 5.9, 8.3, 11.8, 13.2 and 21.7° in powder X-ray diffraction. Also, the Form B crystal of the subject compound provides the DTA curve depicted in FIG. 4, and exhibits an endothermic peak at 169° C., that is 167 to 171° C.

Figure 5:
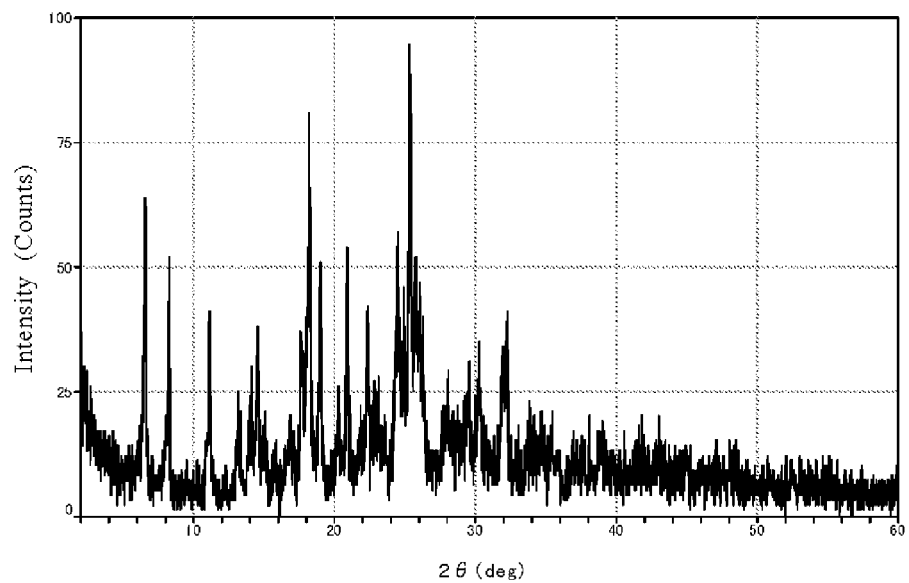
FIG. 5 is a powder X-ray diffraction pattern of the Form E (hydrate) crystal of the subject compound.

As shown in FIG. 5, the Form E (hydrate) crystal of the subject compound exhibits characteristic peaks at diffraction angle 2θ (°) of 6.6, 8.3, 11.1, 14.6 and 18.2° in powder X-ray diffraction. Also, the Form E (hydrate) crystal of the subject compound provides the DTA curve depicted in FIG. 6, and exhibits an endothermic peak at 102° C., that is 100 to 104° C.

Figure 7:
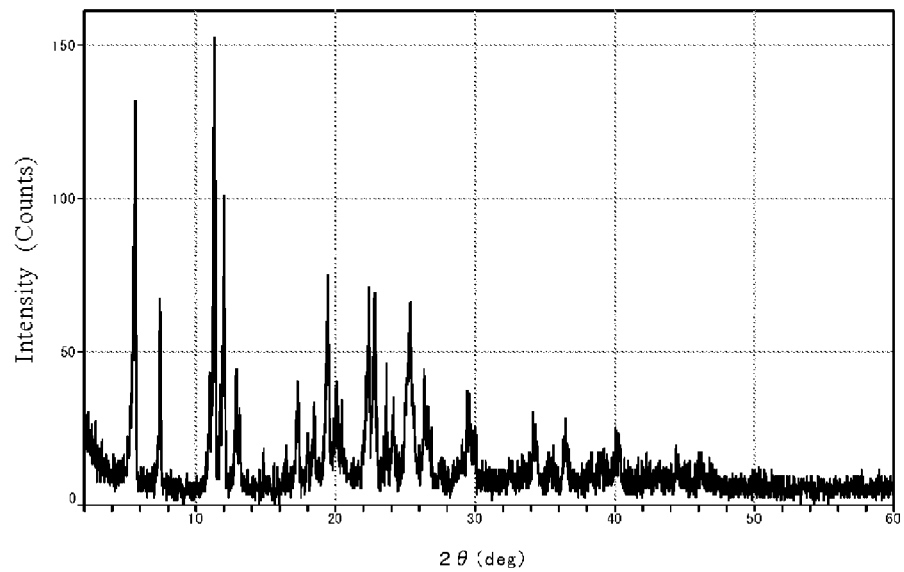
FIG. 7 is a powder X-ray diffraction pattern of the Form A crystal of the subject compound.
Figure 8:
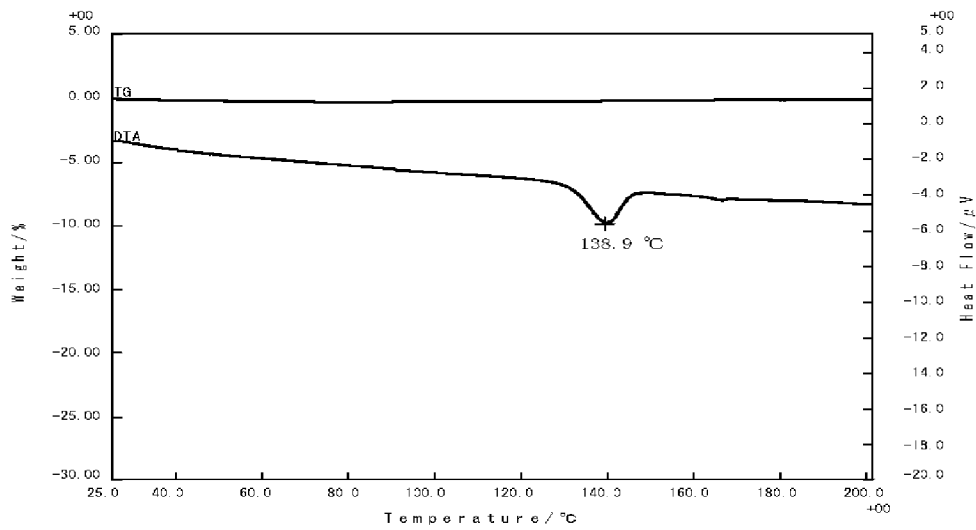
FIG. 8 is a differential thermal analysis curve obtained by thermogravimetric-differential thermal analysis of the Form A crystal of the subject compound.

As shown in FIG. 7, the Form A crystal of the subject compound exhibits characteristic peaks at diffraction angle 2θ (°) of 5.7, 7.4, 11.3 and 12.0° in powder X-ray diffraction. Also, the Form A crystal of the subject compound provides the DTA curve depicted in FIG. 8, and exhibits an endothermic peak at 139° C., that is 137 to 141° C.

Figure 9:
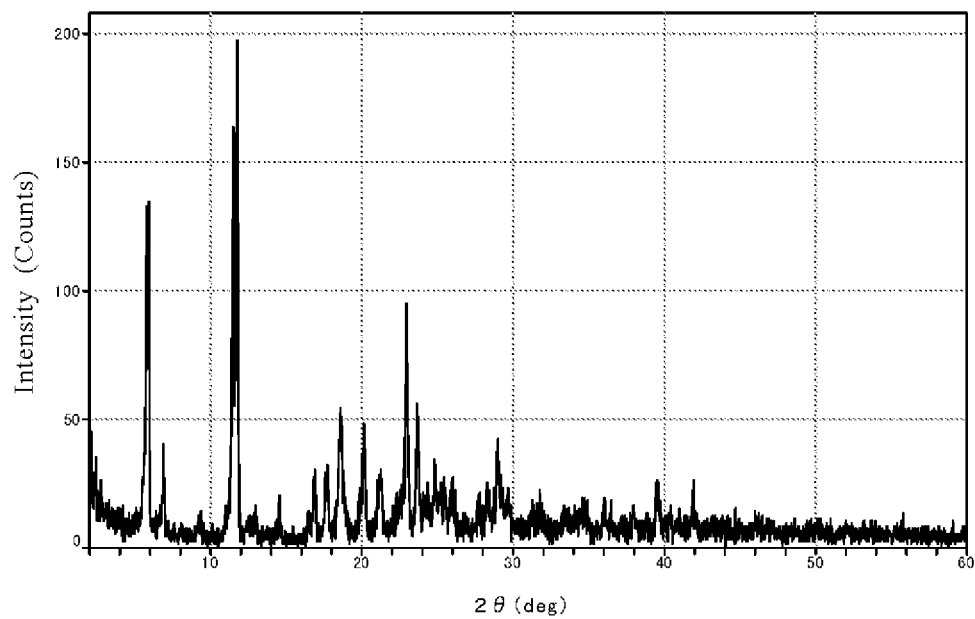
FIG. 9 is a powder X-ray diffraction pattern of the Form D crystal of the subject compound.

As shown in FIG. 9, the Form D crystal of the subject compound exhibits characteristic peaks at diffraction angle 2θ (°) of 5.8, 11.5, 11.8 and 23.0°. Also, the Form D crystal of the subject compound provides the DTA curve depicted in FIG. 10, and exhibits an endothermic peak at 135° C., that is 133 to 137° C.

The powder X-ray diffraction measurement to obtain a powder X-ray diffraction pattern may be carried out under the conditions below by using a powder X-ray diffractometer. A measurement sample is prepared by filling a sample material in a sample plate (material: silicon; depth: 0.2 mm), and leveling out the surface of the sample material.

Conditions of Powder X-Ray Diffraction
 X-ray Source: CuKα radiation
 *using a curved crystal monochromator (graphite)
 Output: 40 kV/50 mA
 Divergence Slit: ½°
 Vertical limiting Slit: 5 mm
 Scattering Slit: ½°
 Receiving Slit: 0.15 mm
 Detector: Scintillation counter
 Scan Mode: 2θ/θ scan, Continuous scan
 Measurement Range (2θ): 2 to 60°
 Scanning Rate (2θ): 4°/min
 Scanning Step (2θ): 0.02°

The endothermic peak means the temperature of the peak top on a DTA curve. The TG-DTA measurement used herein for obtaining the DTA curve may be carried out under conditions below by using a TG-DTA analyzer.

TG-DTA Conditions
 Heating Rate: 5° C./min.
 Atmosphere: nitrogen (flow rate: 50 mL/min)
 Sample Cell: aluminum open cell
 Sample Weight: 4 to 6 mg The Form C crystal of the subject compound can be obtained by dissolving the subject compound in any form in an aromatic solvent to a concentration of 0.1 to 5 mg/mL, preferably 1 to 5 mg/mL, and leaving to stand or stirring the resulting solution at 0 to 30° C. for 1 to 30 days.

The Form C crystal of the subject compound can be obtained by dissolving under heat the subject compound in any form in an alcohol solvent at 50 to 80° C. to a concentration of preferably 10 to 100 mg/mL, more preferably 50 to 80 mg/mL, adding the preliminarily obtained Form C crystal as a seed crystal to the resulting solution, and then stirring the solution at 50 to 80° C. for 1 to 48 hours and further at 0 to 30° C. for 1 to 24 hours.

The Form B crystal of the subject compound can be obtained by dissolving the subject compound in any form in an alcohol solvent to a concentration of preferably 20 to 100 mg/mL, more preferably 25 to 50 mg/mL, and leaving to stand or stirring the resulting solution at 0 to 30° C. for 1 to 30 days.

The Form E (hydrate) crystal of the subject compound can be obtained by adding water in an amount of preferably 10 to 1000 mL, more preferably 3 to 100 mL per 1 g of the amorphous subject compound to obtain suspension, and stirring the suspension at 0° C. to 30° C. for 1 to 30 days.

The Form A crystal of the subject compound can be obtained by dissolving the subject compound in any form in toluene to a concentration of preferably 5 to 20 mg/mL, more preferably 10 to 15 mg/mL, and leaving the resulting solution to stand air-tightly at 0 to 30° C. for 1 to 30 days.

The Form D crystal of the subject compound can be obtained by dissolving the subject compound in any form in an alcohol solvent or ester solvent to a concentration of preferably 5 to 20 mg/mL, more preferably 10 to 15 mg/mL, and leaving to stand or stirring the resulting solution at 0 to 30° C. for 1 to 30 days.

Examples of the above-described aromatic solvent include benzene, chlorobenzene, toluene, xylene and cumene; and toluene or xylene is preferable.

Examples of the above-described alcohol solvent include methanol, ethanol, 1-propanol, 2-propanol, 1-butanol and 2-butanol; and methanol, ethanol or 2-propanol is preferable.

Examples of the above-described ester solvent include ethyl formate, methyl acetate, ethyl acetate, propyl acetate, isopropyl acetate and isobutyl acetate; and methyl acetate, ethyl acetate or propyl acetate is preferable.

The crystal of the subject compound may be used as a pharmaceutical useful for therapies and/or prophylactics of inflammatory bowel disease, allergic dermatitis, multiple sclerosis or leukemia in mammals (e.g., mouse, rat, hamster, rabbit, dog, monkey, bovine, sheep and human). When the crystal of the subject compound is clinically administered as a pharmaceutical, the dose of the crystal may be appropriately selected depending on the symptom, age, body weight, sex, administration method or the like. For example, a dose of 0.01 mg to 5 g per day in case of an injection solution, and a dose of 0.1 mg to 10 g per day in case of an oral preparation are preferably administered to an adult in terms of the effective component, and may be administered at one time or dividedly in several times respectively.

When the crystal of the subject compound is clinically administered as a pharmaceutical, examples of the formulation include oral preparations such as tablets, capsules, granules, powders and syrups; and parenteral preparations such as inhalants, injection solutions, eye drops, nasal sprays, suppositories, ointments, creams, lotions and patches. These formulations may be prepared according to methods commonly used in the field of formulation. In this case, additives commonly used in the field of formulation such as vehicles, stabilizers, preservatives, buffering agents, solubilizers, emulsifiers, diluents and isotonic agents may be admixed appropriately, as necessary. Examples of the pharmaceutically acceptable carrier and diluent used for preparing the above-described formulations include binders (syrups, gelatin, gum arabic, methylcellulose, hydroxypropylcellulose, hydroxypropylmethylcellulose, sorbitol, polyvinylpyrrolidone, polyvinyl alcohol, tragacanth and the like), vehicles (sucrose, lactose, D-mannitol, erythritol, crystalline cellulose, ethyl cellulose, corn starch, calcium phosphate, sorbitol, glycine and the like), disintegrants (partially pregelatinized starch, croscarmellose sodium, crospovidone and low substituted hydroxypropylcellulose), and lubricants (magnesium stearate, polyethylene glycol, talc, silica, sucrose esters of fatty acid and the like).

The Pharmaceutical containing as an effective component the crystals of the subject compound contains the crystals preferably in an amount of 0.001 to 90% by weight, more preferably in an amount of 0.01 to 70% by weight per dosage unit.

To control productivity, compatibility or solubility of pharmaceuticals, the crystal of the subject compound may be blended after being ground. The ground crystals of the subject compound have a particle diameter distribution in which D90 is preferably not more than 1000 μm, and more preferably not more than 100 μm. The term "D90" herein means the particle diameter at the point where the volume which is cumulatively measured from smaller particles reaches 90%, that is, the point where the cumulative frequency of the volume distribution reaches 90%.

The methods of grinding the crystals of the subject compound include grindings with fluid energy mills such as a jet mill; and impact mills such as a hammer mill, a pin mill and a ball mill.

EXAMPLES

Our crystals will now be described concretely by way of Examples, but this disclosure is not restricted to the Examples.

Reference Example 1

Preparation of Amorphous Subject Compound

The subject compound (1 g) prepared by the method described in WO '213 was dissolved in methanol (10 mL) and, after concentrating the resulting solution by an evaporator, the concentrate was dried under reduced pressure by using a vacuum pump for three days to obtain the amorphous subject compound.

Reference Example 2

Preparation of Amorphous Subject Compound

The subject compound (1 g) prepared by the method described in WO '213 was dissolved in tetrahydrofuran (10 mL) and, after concentrating the resulting solution by an evaporator, the concentrate was dried under reduced pressure by using a vacuum pump for one day to obtain the amorphous subject compound.

Reference Example 3

Production of (S)-2-(2,6-dichlorobenzoylamino) pent-4-enoic acid ethyl ester (another name: (S)-2-(2,6-dichlorobenzamido)pent-4-enoic acid ethyl ester)

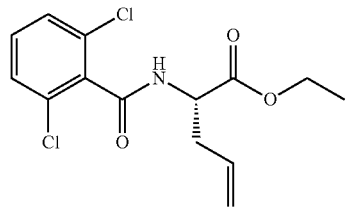 [SMILES: C=CC[C@H](NC(=O)c1c(Cl)cccc1Cl)C(=O)OCC]

L-allylglycine ethyl ester tosylate (100 g) was weighed and added to a 2000-mL flask, and after replacing the atmosphere in the flask with argon, toluene (500 mL) and triethylamine (88.5 mL) were added thereto to obtain suspension. The suspension was cooled to 0° C., and 2,6-dichlorobenzoyl chloride (50.0 mL) and then added dropwise over 20 minutes, followed by stirring the resulting solution at 0° C. for 45 minutes. To the reaction solution, sodium hydrogen carbonate (56 g) dissolved in water (850 mL) was added, and the resulting solution was stirred and then separated into layers. The aqueous layer was extracted with toluene (400 mL), and organic layers were then combined and washed with water (400 mL). The organic layer was concentrated to 285 mL under reduced pressure, and the obtained toluene solution was cooled to 0° C. To the solution, heptane (1000 mL) was added dropwise, and the resulting solution was stirred at 0° C.

for two hours. The crystals were recovered by filtration, and washed with ice-cooled heptane (200 mL), followed by drying under reduced pressure to obtain 88.3 g of (S)-2-(2,6-dichlorobenzoylamino)pent-4-enoic acid ethyl ester (Yield: 88%).

$^1$H NMR (400 MHz, CDCl$_3$) δ 1.31 (3H, t, J=7.1 Hz), 2.66 (1H, m), 2.80 (1H, m), 4.20-4.30 (2H, m), 4.93 (1H, ddd, J=5.4, 5.4, 7.8 Hz), 5.15 (1H, d, J=9.8 Hz), 5.19 (1H, d, J=15.6 Hz), 5.78 (1H, m), 6.41 (1H, br. d, J=5.4 Hz), 7.25-7.34 (3H, m).

Reference Example 4

Production of (S,E)-2-(2,6-dichlorobenzamido)-5-[4-(methyl-pyrimidin-2-ylamino)phenyl]pent-4-enoic acid ethyl ester

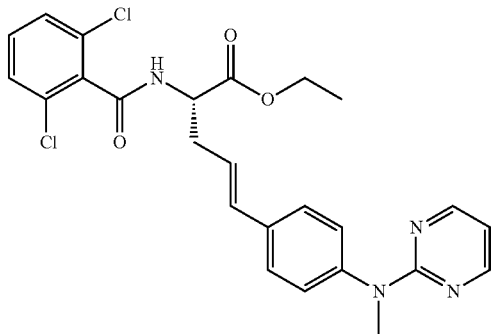 [SMILES: CCOC(=O)[C@H](C/C=C/c1ccc(N(C)c2ncccn2)cc1)NC(=O)c1c(Cl)cccc1Cl]

After replacing the atmosphere in a 500-mL flask with argon, N,N-dimethylformamide (144 mL) and ethanol (16 mL) were added to thereto. Then, (S)-2-(2,6-dichlorobenzoylamino)pent-4-enoic acid ethyl ester (16.0 g) produced in Reference Example 3, N-(4-iodophenyl)-N-methyl-2-pyrimidinylamine (another name: N-(4-iodophenyl)-N-methylpyrimidin-2-amine) (16.5 g) described in WO '213, tetra-n-butylammonium bromide (16.3 g), potassium carbonate (14.0 g) and palladium acetate (230 mg) were successively added to the flask and, after replacing the atmosphere in the system with argon, the resulting solution was stirred at 50° C. for 18 hours. The reaction solution was cooled to room temperature, and water (320 mL) was then added thereto, followed by extraction with ethyl acetate (265 mL). The extract was washed twice with 5% aqueous sodium thiosulfate solution (80 mL), then twice with 5% aqueous sodium chloride solution (80 mL), and then the extract was concentrated under reduced pressure to about 75 g of the solution weight. The procedure in which ethanol (100 mL) was added to the concentrate and the resulting solution was concentrated under reduced pressure to about 75 g, was repeated three times and active carbon (8.0 g) was added to the obtained ethanol solution, followed by stirring at room temperature for 30 minutes. The active carbon was removed by filtration and washed with ethanol (10 mL). To the filtrate, active carbon (4.0 g) was added and, after stirring the resultant at room temperature for 30 minutes, the active carbon was removed by filtration, and washed with ethanol (10 mL). The filtrate was concentrated under reduced pressure to 78 g, and the obtained ethanol solution heated to 50° C. After adding distilled water (30 mL) dropwise to the solution, the resulting solution was cooled to room temperature and further cooled to 0° C., followed by stirring the solution for one hour. The crystals were removed by filtration, washed with ice-cooled mixture of ethanol and water at a ratio of 2:1 (20 mL), and then dried under reduced pressure to obtain 18.3 g of (S,E)-2-(2,6-dichlorobenzamido)-5-[4-(methyl-pyrimidin-2-ylamino)phenyl]pent-4-enoic acid ethyl ester (Yield: 73%).

$^1$H NMR (400 MHz, CDCl$_3$) δ 1.32 (3H, t, J=7.1 Hz), 2.84 (1H, m), 2.97 (1H, m), 3.51 (3H, s), 4.25 (1H, m), 4.28 (1H, m), 5.01 (1H, m), 6.11 (1H, dt, J=15.6, 7.6 Hz), 6.48 (1H, m), 6.52 (1H, d, J=15.6 Hz), 6.58 (1H, t, J=4.6 Hz), 7.24-7.37 (7H, m), 8.33 (2H, d, J=4.6 Hz).

Example 1

Production of Form C Crystal of Subject Compound

Figure 2:
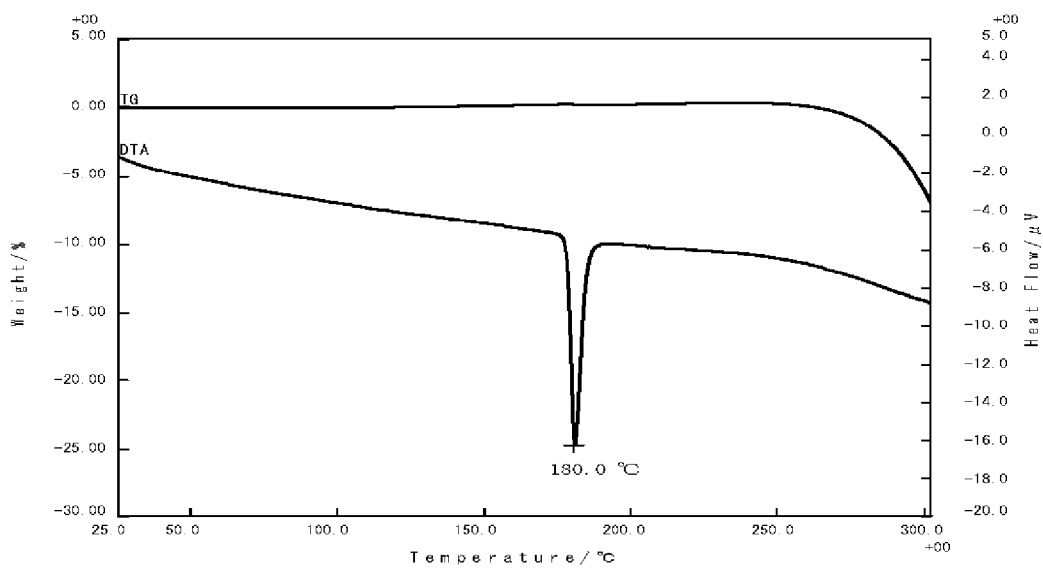
FIG. 2 is a differential thermal analysis curve obtained by thermogravimetric-differential thermal analysis of the Form C crystal of the subject compound.

The amorphous subject compound (30 mg) prepared in Reference Example 1 was weighted and added to a vial made of borosilicate glass, and toluene (15 mL) was added thereto, followed by stirring the resultant at room temperature to dissolve the compound. The resulting solution was left to stand at room temperature under open conditions. After confirming the precipitates, solvent was removed with a Pasteur pipette and the precipitates were dried under reduced pressure by using a vacuum pump for 30 minutes to obtain white powder of the captioned crystal. For the obtained crystals, powder X-ray diffraction measurement by using powder X-ray diffractometer (Rigaku; 2200/RINT ultima $^+$PC) and TG-DTA by using TG-DTA analyzer (Rigaku; TG810D) were carried out. The results of these measurements are shown in FIGS. 1 and 2.

Diffraction angle 2θ: 17.1, 17.7, 18.7, 19.9, 21.0°
Endothermic peak: 180° C.

Example 2

Production of Form C Crystal of Subject Compound

To a 500 mL flask, (S,E)-2-(2,6-dichlorobenzamido)-5-[4-(methyl-pyrimidin-2-ylamino)phenyl]pent-4-enoic acid ethyl ester (5.50 g) prepared in Reference Example 4 was weighted and added, and 4 mol/L of hydrochloric acid (110 mL) was added thereto, followed by stirring the obtained suspension at 50° C. for 6 hours. After cooling the reaction solution to 0° C., ethanol (50 mL) was added and sodium hydroxide (18.5 g) dissolved in water (50 mL) was further added thereto, followed by stirring the resulting reaction solution at room temperature for 20 minutes. The reaction solution was cooled to 0° C. and, after adding 4 mol/L of hydrochloric acid thereto to adjust pH of the solution to about 3, the resulting solution was extracted with ethyl acetate (150 mL). The extract was washed with water (100 mL) and concentrated under reduced pressure. To the concentrate, ethanol (100 mL) was added and, after concentrating the resultant to 18 g of the solution weight, heptane (15 mL) was added, followed by stirring the solution at room temperature. The crystals were removed by filtration and dried under reduced pressure to obtain 4.62 g of the crude crystals (Yield: 89%).

The obtained crude crystals (4.20 g) was weighted and added to a 200 mL flask and 2-propanol (56 mL) was added thereto, followed by heating the resulting solution under stirring. Cooling of the solution was started after confirming dissolution at 73° C. Seed crystals (190 mg) were added thereto at 70° C., the solution was cooled to 55° C. and then stirred at 55° C. for 12 hours. Then, the solution was cooled to 0° C. and stirred at 0° C. for 18 hours. The crystals were removed by filtration, washed with 2-propanol and dried to obtain 3.85 g of Form C crystals of the subject compound (Yield: 92%). For the obtained crystals, powder X-ray diffraction measurement and TG-DTA were carried out, and it was confirmed that the results were consistent with FIGS. 1 and 2.

Example 3

Production of Form B Crystal of Subject Compound

Figure 4:
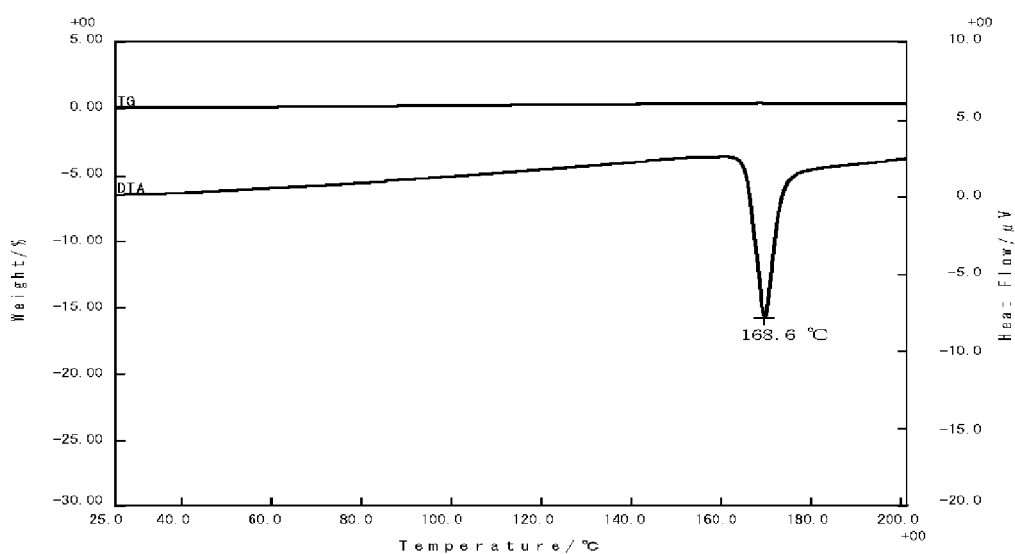
FIG. 4 is a differential thermal analysis curve obtained by thermogravimetric-differential thermal analysis of the Form B crystal of the subject compound.

The amorphous subject compound (30 mg) prepared in Reference Example 2 was weighted and added to a vial made of borosilicate glass and methanol (1.1 mL) was added thereto, followed by stirring the resulting mixture at room temperature to dissolve the compound. The mixture was left to stand at room temperature under open conditions. After confirming the precipitates, solvent was removed with a Pasteur pipette and the precipitates were dried under reduced pressure by using a vacuum pump for 30 minutes to obtain white powder of Form B of the subject compound. For the obtained crystals, powder X-ray diffraction measurement and TG-DTA were carried out. The results of these measurements are shown in FIGS. 3 and 4.

Diffraction angle 2θ: 5.9, 8.3, 11.8, 13.2, 21.7°
Endothermic peak: 169° C.

Example 4

Production of Form E (Hydrate) Crystal of Subject Compound

Figure 6:
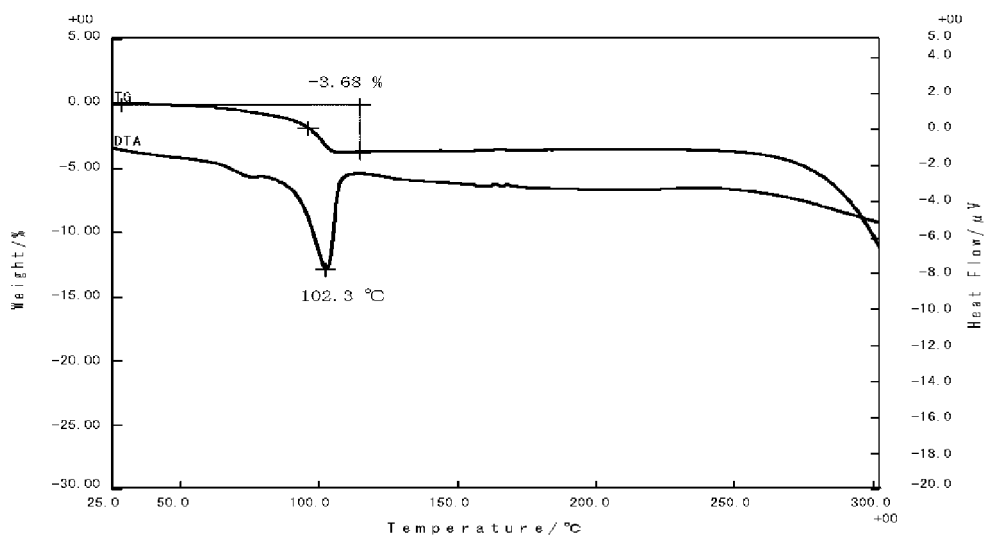
FIG. 6 is a differential thermal analysis curve obtained by thermogravimetric-differential thermal analysis of the Form E (hydrate) crystal of the subject compound.

The amorphous subject compound (30 mg) prepared in Reference Example 1 was weighted and added to a vial made of borosilicate glass and water (10 mL) was added thereto, followed by stirring the resulting suspension overnight. The solids were removed by filtration from the suspension to obtain white powder of Form E (hydrate) of the subject compound. For the obtained crystals, powder X-ray diffraction measurement and TG-DTA were carried out. The results of these measurements are shown in FIGS. 5 and 6.

Diffraction angle 2θ: 6.6, 8.3, 11.1, 14.6, 18.2°
Endothermic peak: 102° C.

Example 5

Production of Form A Crystal of Subject Compound

The amorphous subject compound (30 mg) prepared in Reference Example 2 was weighted and added to a vial made of silicate glass and toluene (3 mL) was added thereto, followed by stirring the resulting mixture at room temperature to dissolve the compound. Then, the vial made of borosilicate glass was capped and left to stand air-tightly at room temperature. After confirming the precipitates, solvent was removed with a Pasteur pipette and the precipitates were dried under reduced pressure by using a vacuum pump for 30 minutes to obtain white powder of Form A of the subject compound. For the obtained crystals, powder X-ray diffraction measurement and TG-DTA were carried out. The results of these measurements are shown in FIGS. 7 and -8.

Diffraction angle 2θ: 5.7, 7.4, 11.3, 12.0°
Endothermic peak: 139° C.

Example 6

Production of Form D Crystal of Subject Compound

Figure 10:
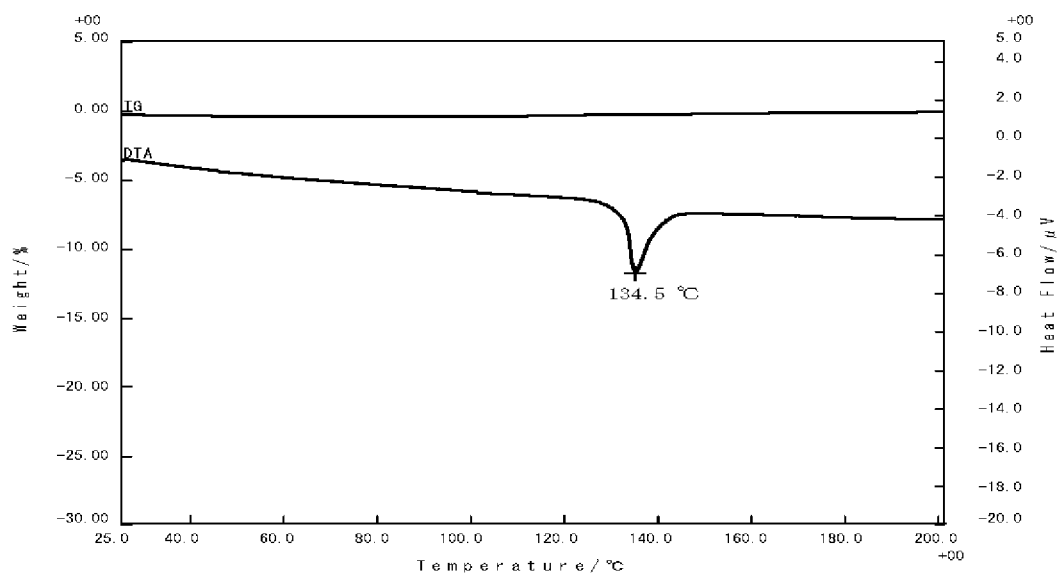
FIG. 10 is a differential thermal analysis curve obtained by thermogravimetric-differential thermal analysis of the Form D crystal of the subject compound.

The amorphous subject compound (30 mg) prepared in Reference Example 1 was weighted and added to a vial made of borosilicate glass and ethanol (2 mL) was added thereto, followed by stirring the resulting mixture at room temperature to dissolve the compound. The mixture was left to stand at room temperature under open conditions. After confirming the precipitates, solvent was removed with a Pasteur pipette and the precipitates were dried under reduced pressure by using a vacuum pump for 30 minutes to obtain white powder of Form D of the subject compound. For the obtained crystals, powder X-ray diffraction measurement and TG-DTA were carried out. The results of these measurements are shown in FIGS. 9 and 10.

Diffraction angle 2θ: 5.8, 11.5, 11.8, 23.0°
Endothermic peak: 135° C.

Test Example 1

Evaluation of Moisture Absorption

Measurement Conditions of Equilibrium Moisture Regain
  Sample Amount: 5 to 12 mg
  Measuring Temperature: 25° C.
  Equilibrium Weight/time: 0.01 wt %/5 minutes
  Maximum Equilibration Time: 180 minutes
  Measurement Range: 5% relative humidity-95% relative humidity-5% relative humidity
  Measurement Interval: 5% relative humidity To evaluate whether the crystal form changes or not, the powder X-ray diffraction measurement was carried out for each crystal of Form A, Form B, Form C, Form D and Form E (hydrate) obtained after the evaluation test of moisture absorption. The results are shown in Table 1. Only for the Form A crystal, the measurement range (2θ) of the powder X-ray diffraction measurement was changed to 2 to 35°, and the measurement was carried out at 25° C., 90% relative humidity. A humidity generator (HUM-1A; manufactured by Rigaku) was used to control humidity.

TABLE 1

| Crystal form | Form A | Form B | Form C | Form D | Form E |
|---|---|---|---|---|---|
| Weight increase[1] | 3.4% | 1.9% | less than 0.1% | 1.0% | 0.4% |
| Change in crystal form | changed[2] | not changed | not changed | not changed | not changed |

[1]The weight increase means one observed when the relative humidity was increased from 5% to 95%.
[2]The crystal was transferred to a hydrate different from the Form E (hydrate) crystal when the relative humidity was increased from 5% to 95%.

As shown in Table 1, as for crystals of the Form B, Form C, Form D and Form E (hydrate) of the subject compound, the weight increases due to humidification were not substantially changed, and the crystal forms were not changed. These results revealed that the crystals of Form B, Form C, Form D and Form E (hydrate) of the subject compound are excellent in physical stability.

Test Example 2

Evaluation of Solid-State Stability

The amorphous form, and the crystals of Form A, Form B, Form C, Form D and Form E (hydrate) of the subject compound were stored air-tightly at 60° C. for four weeks, and the purities thereof before and after the storage were measured by high performance liquid chromatography (hereinafter referred to as "HPLC") under the following conditions. The powder X-ray diffraction measurement and TG-DTA were carried out to evaluate whether the crystal forms were changed or not due to the storage. The results are shown in Table 2. Aqueous sodium dihydrogen phosphate solution in a concentration of 20 mmol/L (hereinafter referred to as "aqueous SDP solution") used to prepare a mobile phase of HPLC was prepared by adding distilled water (3 L) to weighed sodium dihydrogen phosphate dihydrate (9.36 g) and stirring the resulting solution to dissolve the dihydrate. An analytical sample of HPLC was prepared by weighing and adding each crystal (1.75 mg) of the subject compound to a 10-mL measuring flask respectively; adding acetonitrile (2 mL) thereto to dissolve the crystal; and then adding aqueous SDP solution thereto to a total volume of 10 mL.

HPLC Conditions
  Detection Wavelength: 210 nm
  Column: YMC-Pack Pro C18 AS-303
  Mobile Phase A: aqueous SDP solution/acetonitrile=80:20 (v/v)
  Mobile Phase B: acetonitrile/aqueous SDP solution=70:30 (v/v)
  Composition of Mobile Phase B: 0 to 60 minutes: 0→100%
  60 to 65 minutes: 100%,
  65 to 66 minutes: 100→0%,
  66 to 75 minutes: 0%
  Flow rate: 1.0 mL/min
  Column Temperature: 40° C.
  Amount of Injected Sample: 20 μL X-ray diffraction measurement and TG-DTA were carried out to evaluate whether the crystal form was changed or not due to storage.

Phosphate buffer in a concentration of 20 mmol/L (pH 3.9) (hereinafter referred to as "Buffer X") used to prepare a mobile phase of HPLC was prepared by adding 20 mmol/L of aqueous phosphoric acid solution to 20 mmol/L of aqueous potassium dihydrogen phosphate solution. 20 mmol/L of the aqueous potassium dihydrogen phosphate solution was prepared by adding the weighed potassium dihydrogen phosphate (8.2 g) to distilled water (3 L), and stirring the resulting solution to dissolve the phosphate, and 20 mmol/L of the aqueous phosphoric acid solution was prepared by adding phosphoric acid (1.4 mL) to distilled water (1 L), and mixing the resulting solution under stirring.

Phosphate buffer in a concentration of 20 mmol/L (pH 7.0) (hereinafter referred to as "Buffer Y") used to prepare an analytical sample of HPLC was prepared by adding 20 mmol/L of aqueous phosphoric acid solution to 20 mmol/L of aqueous dipotassium hydrogen phosphate solution. 20 mmol/L of aqueous dipotassium hydrogen phosphate solution was prepared by adding the weighed dipotassium hydrogen phosphate (3.5 g) to distilled water (1 L), and stirring the resulting solution.

Further, the analytical sample of HPLC was prepared by weighing and adding the Form C crystals of the subject compound (10 mg) to a 50-mL measuring flask, and adding a mixture of Buffer Y and acetonitrile at a ratio of 80:20 to a total amount of 50 mL.

TABLE 2

| | | Crystal Form | | | | |
|---|---|---|---|---|---|---|
| | | Form A | Form B | Form C | Form D | Form E | Amorphous |
| Purity [%] | Initial value | 97.3 | 99.8 | 98.9 | 98.0 | 96.6 | 95.8 |
| | After 4 weeks | 97.5 | 99.8 | 98.9 | 98.0 | 96.9 | 92.0 |
| Decomposition product increased by not less than 0.15% after 4 weeks | | nothing | nothing | nothing | nothing | nothing | 8 different products[1] |
| Crystal form after 4 weeks | | Form B | Form B | Form C | Mixed crystals[2] | Form E | Amorphous |

[1]The increased amount of each decomposition product increased by not less than 0.15% was 0.49% for a decomposition product at 0.9 of the relative retention time (hereinafter referred to as "RRT"), 0.20% for a decomposition product at RRT 1.0, 0.23% for a decomposition product at RRT 1.1, 0.20% for a decomposition product at RRT 1.2, 0.15% for a decomposition product at RRT 1.6, 1.30% for a decomposition product at RRT 1.8, and 0.22% and 0.20% for two decomposition products at RRT 2.3. The "RRT" is calculated by dividing the retention time of the decomposition product in HPLC chromatogram by the retention time of the subject compound in HPLC chromatogram.
[2]Mixed crystals of Form B, Form C, Form D and Form E.

As shown in Table 2, the purities of the crystals of Form A, Form B, Form C, Form D and Form E (hydrate) of the subject compound were not substantially changed. These results revealed that the crystals of Form A, Form B, Form C, Form D and Form E (hydrate) of the subject compound are excellent in chemical stability compared to the amorphous form. The crystal forms of the Form B, Form C and Form E (hydrate) of the subject compound were not changed due to storage. These results revealed that the crystals of Form B, Form C and Form E (hydrate) of the subject compound are excellent also in physical stability.

Test Example 3

Storage Stability Test (Accelerated Testing) of Form C Crystal

The Form C crystals of the subject compound were stored under acceleration conditions (40° C., 75% relative humidity) air-tightly or under open conditions for six months, and the purities of the crystals before and after the storage were measured by HPLC under conditions below. The powder In "the Guideline on Stability Testing" based on the agreements in International Conference on Harmonisation of Technical Requirements for Registration of Pharmaceuticals for Human Use (ICH), to evaluate the stability of the quality required to maintain the effectiveness and safety of the pharmaceutical, the accelerated testing (40° C., 75% relative humidity, six months) is set as a test to predict chemical influences when stored for a long time under conventional storage conditions (for example, 25° C.) and, simultaneously, to confirm the effect of short term excursions outside the storage condition which excursions may be occurred during shipping and the like. The data obtained by the accelerated testing are indispensable in the application for approval of pharmaceuticals.

HPLC Conditions
  Detection Wavelength: 210 nm
  Column: YMC-Pack Pro C18
    AS12S05-2546WT
  Mobile Phase A: buffer X/acetonitrile=80:20 (v/v)
  Mobile Phase B: acetonitrile/buffer X=70:30 (v/v)
  Composition of Mobile Phase B: 0 to 80 minutes: 0→100%

80 to 85 minutes: 100%
85 to 86 minutes: 100→0%
86 to 95 minutes: 0%
Flow Rate: 1.0 mL/min
Column Temperature: 40° C.
Amount of Injected Sample: 20 μL

TABLE 3

| Storage conditions | | 40° C., 75% relative humidity, air-tightly, 6 months | 40° C., 75% relative humidity, open condition, 6 months |
|---|---|---|---|
| Purity [%] | Initial value | 99.5 | 99.5 |
| | After 6 months | 99.5 | 99.4 |
| Decomposition product increased by not less than 0.15% after 6 months | | Nothing | Nothing |
| Crystal form after 6 months | | Form C | Form C |

As a result, as shown in Table 3, the purity of the subject compound after the Form C crystals were stored under accelerate conditions air-tightly or under open conditions for six months was not substantially changed compared to the initial purity. The crystal form of the Form C crystals of the subject compound was not changed due to storage. Since the quality of the Form C crystal was not clearly changed chemically and physically in the accelerated testing, the Form C crystal was revealed to be very stable and excellent as an effective component of pharmaceuticals in view of storage and distribution. Further, it was revealed that the Form C crystal was excellent in physical stability in that the crystal form thereof was not transferred to the another form even in solvents (e.g., toluene, methanol, 2-propanol usable in the crystallization of the subject compound).

Example 7

Production of Quick Release Tablets Using Form C Crystal

The pin milled product of the Form C crystals of the subject compound (14.17 g), D-mannitol (35.98 g; Roquette Japan K.K.; PEARLITOL (registered trademark) 50C), crystalline cellulose (42.5 g; Asahi Kasei Corp.; CEOLUS (registered trademark) grade PH-101), partially pregelatinized starch (42.5 g; Asahi Kasei Corp.; grade PCS), hydroxypropyl cellulose (8.5 g; Nippon Soda; grade L), meglumine (8.5 g; Merck) and magnesium oxide (8.5 g; Tomita Pharmaceutical Co., Ltd.) were fed to a mixing granulator (Nara Machinery Co., Ltd.; NMG-1L), and after mixing the resultant, water (32.2 g) was sprayed to carry out stirring granulation. The granulated powders were dried in an oven at 40° C. for two hours to obtain granules. The obtained granules were subjected to sieving by COMIL (Powrex Corporation; QC-197S; mesh 1143 μm; speed of rotation 2000 rpm) to obtain size-selected granules. To the obtained size-selected granules, croscarmellose sodium (8.5 g; FMC Biopolymer; Ac-Di-Sol (registered trademark)) and magnesium stearate (0.85 g; Taihei Chemical Industrial) were added and mixed by using V-blender (Tsutsui Scientific Instruments Co., Ltd., S-3) to obtain granules for tableting. The obtained granules were tabletted with a rotary tableting machine (KIKUSUI SEISAKUSHO LTD.; Correct 19) using a round-shaped punch and die with a diameter of 8 mm to obtain 180 mg of plain tablets containing 15 mg of the subject compound, 38.1 mg of D-mannitol, 45 mg of crystalline cellulose, 45 mg of partially pregelatinized starch, 9 mg of hydroxypropylcellulose, 9 mg of meglumine, 9 mg of magnesium oxide, 9 mg of croscarmellose sodium, and 0.9 mg of magnesium stearate per a tablet.

Example 8

Production of Quick Release Tablets Using Form C Crystal

The jet milled product of the Form C crystals of the subject compound (41.67 g), lactose (230.83 g; DMV International; Pharmatose (registered trademark) 200M), crystalline cellulose (175 g; Asahi Kasei Corp.; CEOLUS (registered trademark) grade PH-101) and hydroxypropyl cellulose (25 g; Nippon Soda; grade L) were fed to a mixing granulator (Nara Machinery Co., Ltd.; NMG-3L), and after mixing the resultant, water (95 g) was sprayed to carry out stirring granulation. The granulated powders were dried in an oven at 40° C. for two hours to obtain granules. The obtained granules were sieved with mesh size of 1 mm, croscarmellose sodium (25 g; FMC Biopolymer; Ac-Di-Sol (registered trademark)) and magnesium stearate (2.5 g; Taihei Chemical Industrial) were added thereto, and mixed by using V-blender (Tsutsui Scientific Instruments Co., Ltd.; S-3) to obtain granules for tableting. The obtained granules were tabletted with a rotary tableting machine (KIKUSUI SEISAKUSHO LTD.; Correct 19) using a round-shaped punch and die with a diameter of 8 mm to obtain 180 mg of plain tablets containing 15 mg of the subject compound, 83.1 mg of lactose, 63 mg of crystalline cellulose, 9 mg of hydroxypropyl cellulose, 9 mg of croscarmellose sodium and 0.9 mg of magnesium stearate per a tablet.

Example 9

Production of Quick Release Tablets Using Form C Crystal

The jet milled product of the Form C crystals of the subject compound (107.14 g), lactose (165.36 g; DMV International; Pharmatose (registered trademark) 200M), crystalline cellulose (175 g; Asahi Kasei Corp.; CEOLUS (registered trademark) grade PH-101) and hydroxypropyl cellulose (25 g; Nippon Soda; grade L) were fed to a mixing granulator (Nara Machinery Co., Ltd.; NMG-3L), and after mixing, water (100 g) was sprayed to carry out stirring granulation. The granulated powders were dried in an oven at 40° C. for two hours to obtain granules. The obtained granules were sieved with mesh size of 1 mm, croscarmellose sodium (25 g; FMC Biopolymer; Ac-Di-Sol (registered trademark)) and magnesium stearate (5 g; Taihei Chemical Industrial) were added thereto, and mixed by using V-blender (Tsutsui Scientific Instruments Co., Ltd.; S-3) to obtain granules for tableting. The obtained granules were tabletted with a rotary tableting machine (KIKUSUI SEISAKUSHO LTD.; Correct 19) using a round-shaped punch and die with a diameter of 7 mm to obtain 140.7 mg of plain tablets. The obtained plain tablets were placed in a film coating machine (Freund Corporation; HICOATER MINI), and sprayed with a liquid in which OPADRY (registered trademark) OY-7300 (Japan Colorcon; mixture of hydroxypropylmethylcellulose 2910, titanium oxide and polyethylene glycol 400), red ferric oxide (KISHI KASEI CO., LTD.) and yellow ferric oxide (KISHI KASEI CO., LTD.) were dispersed, thereby obtaining film-coated tablets containing 30 mg of the subject compound, 46.3 mg of lactose, 49 mg of crystalline cellulose, 7 mg of hydroxypropylcellulose, 7 mg of croscarmellose sodium, 1.4 mg of magnesium stearate, 3.88 mg of OY-7300, 0.08 mg of red ferric oxide and 0.03 mg of yellow ferric oxide per a tablet.

Example 10

Production of Quick Release Tablets Using Form C Crystal

The jet milled product of the Form C crystals of the subject compound (2.86 g), lactose (2662.9 g; DMV International; Pharmatose (registered trademark) 200M) and crystalline cellulose (1000 g; Asahi Kasei Corp.; CEOLUS (registered trademark) grade PH-101) were placed in a fluid bed granulator/dryer (Freund Corporation; FLO-5), and granulated by spraying an aqueous solution of 7% (wt./v) hydroxypropylcellulose (1633 g; Nippon Soda; grade L) under fluidization, and thereafter dried to obtain granules. The obtained granules were subjected to sieving by COMIL (Powrex Corporation; QC-197S; mesh 1575 nm; speed of rotation 2000 rpm) to obtain size-selected granules. To the obtained size-selected granules, croscarmellose sodium (200 g; FMC Biopolymer; Ac-Di-Sol (registered trademark)) and magnesium stearate (20 g; Taihei Chemical Industrial) were added, and mixed by using V-blender (Dalton Co., Ltd, DV-1-10) to obtain granules for tableting. The obtained granules were tabletted with a rotary tableting machine (KIKUSUI SEISAKUSHO LTD.; Correct 19) using a round-shaped punch and die with a diameter of 7 mm to obtain 140 mg of plain tablets. The obtained plain tablets were placed in a film coating machine (Freund Corporation; HICOATER MINI), and sprayed with a liquid in which OPADRY (registered trademark) OY-7300, red ferric oxide (KISHI KASEI CO., LTD.) and yellow ferric oxide (KISHI KASEI CO., LTD.) were dispersed, thereby obtaining film-coated tablets containing 0.1 mg of the subject compound, 93.2 mg of lactose, 35 mg of crystalline cellulose, 4 mg of hydroxypropylcellulose, 7 mg of croscarmellose sodium, 0.7 mg of magnesium stearate, 3.88 mg of OY-7300, 0.08 mg of red ferric oxide and 0.03 mg of yellow ferric oxide per a tablet.

The particle sizes of the milled Form C crystals of the subject compound used in Examples 7 to 10 were measured by using "Microtrac particle size analyzer" (Nikkiso Co., Ltd.; 9220FRA; wet process). The particle size distributions of the milled Form C crystals of the subject compound were D10: 7.0 μm, D50: 21.9 μm, D90: 56.4 μm for a pin milled product; and D10: 1.7 μm, D50: 3.4 μm, D90: 5.8 μm, or D10: 2.1 μm, D50: 3.9 μm, D90: 6.6 μm for a jet milled product. It was confirmed by powder X-ray diffraction measurement and TG-DTA that no change in the crystal form due to the above milling occurred.

Test Example 4

Evaluation of Storage Stability of Formulations

Tablets obtained in Examples 7 to 10 were stored at 40° C. and 75% relative humidity air-tightly for three months, and the purities thereof before and after the storage were measured by HPLC under the conditions below. The results are shown in Table 4. As the analytical sample for HPLC, a supernatant was used which was obtained by adding 10 tablets or one tablet to a mixture of buffer Y and acetonitrile at a mixing ratio of 80:20 to a concentration of the subject compound of 50 or 300 μg/mL, and stirring and centrifuging the resultant.

HPLC Conditions
Detection Wavelength: 210 nm
Column: YMC-Pack Pro C18
AS 12S05-2546WT
Mobile Phase A: buffer X/acetonitrile=80:20 (v/v)
Mobile Phase B: acetonitrile/buffer X=70:30 (v/v)
Composition of Mobile Phase B: 0 to 80 minutes: 0→100%
80 to 85 minutes: 100%
85 to 86 minutes: 100→0%
86 to 95 minutes: 0%
Flow Rate: 1.0 mL/min
Column Temperature: 40° C.
Amount of Injected Sample: 20 μL (concentration of the subject compound is 300 μg/mL), or 80 μL (concentration of the subject compound is 50 μg/mL)

TABLE 4

| | | Example 7 | Example 8 | Example 9 | Example 10 |
|---|---|---|---|---|---|
| Purity [%] | Initial value | 98.9 | 98.9 | 99.8 | 99.6 |
| | After storage of 3 months | 98.9 | 99.0 | 99.7 | 99.6 |

Even though some crystals are chemically stable as effective components of pharmaceuticals, the crystals may be destabilized due to contact with various additives in a final form of pharmaceuticals such as tablets, and may adversely affect maintenance of effectiveness and safety of the pharmaceuticals. However, as shown in Table 4, for all the tablets containing the Form C crystals of the subject compound as effective components, the purities of the crystals after stored air-tightly under accelerated conditions for three months were not substantially changed compared to the initial purities. These results revealed that the Form C crystal of the subject compound is excellent in chemical stability even after the crystals are formulated via a fine grinding step.

Industrial Availability

The crystal of the subject compound may be used as a pharmaceutical, in particular, a therapeutic or prophylactic agent for inflammatory bowel disease, allergic dermatitis, multiple sclerosis or leukemia in the medical field.

The invention claimed is:

1. A crystal of (S,E)-2-(2,6-dichlorobenzamido)-5-[4-(methyl-pyrimidin-2-ylamino)phenyl]pent-4-enoic acid.

2. The crystal according to claim 1, which exhibits peaks at 2θ (°) of 17.1, 17.7, 18.7, 19.9 and 21.0° in powder X-ray diffraction.

3. The crystal according to claim 2, which exhibits an endothermic peak in the range of 178 to 182° C. in thermogravimetric-differential thermal analysis.

4. The crystal according to claim 1, which exhibits peaks at 2θ (°) of 5.9, 8.3, 11.8, 13.2 and 21.7° in powder X-ray diffraction.

5. The crystal according to claim 4, which exhibits an endothermic peak in the range of 167 to 171° C. in thermograyimetric-differential thermal analysis.

6. The crystal according to claim 1, which exhibits peaks at 2θ (°) of 6.6, 8.3, 11.1, 14.6 and 18.2° in powder X-ray diffraction.

7. The crystal according to claim 6, which exhibits an endothermic peak in the range of 100 to 104° C. in thermogravimetric-differential thermal analysis.

8. The crystal according to claim 1, which is a non-solvate or a hydrate.

9. A pharmaceutical comprising as an effective component said crystal according to claim 1.

10. A therapeutic or prophylactic agent for inflammatory bowel disease, allergic dermatitis, multiple sclerosis or leukemia, comprising as an effective component said crystal according to claim 1.

* * * * *